United States Patent
Zha et al.

(10) Patent No.: US 12,191,551 B2
(45) Date of Patent: Jan. 7, 2025

(54) SINGLE-INPUT TO N-OUTPUT MICROWAVE SYSTEM INCLUDING MULTIPLE BAND-PASS FILTERS AND MULTIPLE ACCELERATORS CONFIGURED FOR SELECTIVE IRRADIATION AT DIFFERENT ANGLES

(71) Applicant: Tsinghua University, Beijing (CN)

(72) Inventors: Hao Zha, Beijing (CN); Jiaru Shi, Beijing (CN); Focheng Liu, Beijing (CN); Huaibi Chen, Beijing (CN)

(73) Assignee: TSINGHUA UNIVERSITY, Beijing (CN)

( * ) Notice: Subject to any disclaimer, the term of this patent is extended or adjusted under 35 U.S.C. 154(b) by 907 days.

(21) Appl. No.: 17/287,470

(22) PCT Filed: Oct. 12, 2020

(86) PCT No.: PCT/CN2020/120462
§ 371 (c)(1),
(2) Date: Apr. 21, 2021

(87) PCT Pub. No.: WO2022/052200
PCT Pub. Date: Mar. 17, 2022

(65) Prior Publication Data
US 2022/0086966 A1    Mar. 17, 2022

(30) Foreign Application Priority Data
Sep. 14, 2020   (CN) .......................... 202010961150.4

(51) Int. Cl.
*H01P 1/213*   (2006.01)
*H05B 6/66*    (2006.01)
*A61N 5/02*    (2006.01)

(52) U.S. Cl.
CPC ............ *H01P 1/213* (2013.01); *H01P 1/2138* (2013.01); *H05B 6/66* (2013.01); *A61N 5/02* (2013.01); *H05B 2206/044* (2013.01)

(58) Field of Classification Search
CPC ........................................................ H01P 1/213
(Continued)

(56) References Cited

U.S. PATENT DOCUMENTS 5,748,057 A * 5/1998 De Los Santos ..... H01P 1/2005
                                                      333/202
2006/0114082 A1  6/2006 Hidalgo Carpintero et al.
(Continued)

OTHER PUBLICATIONS

EPO, Extended European Search Report for EP Application No. 20873359.2, Aug. 10, 2022.

*Primary Examiner* — Benny T Lee
(74) *Attorney, Agent, or Firm* — Hodgson Russ LLP

(57) ABSTRACT

The present disclosure provides a microwave transmission method and a single-input multiple-output waveguide microwave system based on frequency control, an electronic device. The method includes: adjusting frequency of an input microwave, each of different input microwaves with different frequencies being input microwave of the single-input multi-output waveguide microwave system; assigning the input microwave to a target output port among multiple output ports of the single-input multiple-output waveguide microwave system, according to the frequency of the input microwave; and performing microwave output through the target output port.

17 Claims, 4 Drawing Sheets

(58) Field of Classification Search
USPC .......................................................... 333/126
See application file for complete search history.

(56) References Cited

U.S. PATENT DOCUMENTS

2009/0086889 A1    4/2009   Hashemi et al.
2011/0317714 A1   12/2011   Arias et al.
2018/0091244 A1*   3/2018   Abdo ...................... H01P 1/213

\* cited by examiner

SINGLE-INPUT TO N-OUTPUT MICROWAVE SYSTEM INCLUDING MULTIPLE BAND-PASS FILTERS AND MULTIPLE ACCELERATORS CONFIGURED FOR SELECTIVE IRRADIATION AT DIFFERENT ANGLES

CROSS-REFERENCE TO RELATED APPLICATIONS

This application is a U.S. national phase application of International Application No. PCT/CN2020/120462, filed on Oct. 12, 2020, which claims priority to Chinese Patent Application No. 202010961150.4, filed on Sep. 14, 2020, the entire disclosures of which are incorporated by reference herein.

TECHNICAL FIELD

The present disclosure relates to a field of microwave transmission technologies, and more particularly, to a microwave transmission method and a single-input multiple-output waveguide microwave system based on frequency control, an electronic device.

BACKGROUND

In recent years, rapid development of radiotherapy technologies, more particularly, technologies aimed at precise conformation, has greatly reduced side effects of the radiotherapy, expanded scope of radiotherapy indications, and put forward new requirements for medical accelerators. Intensity modulated radiation therapy with a single irradiation field may achieve conformation in a two-dimensional plane in a single direction, but cannot meet conformal requirements for dose distribution in three-dimensional space. For 3-D conformal requirements, most radiotherapy systems employ an irradiation mode with multi-angle and multi-irradiation field. Besides, industrial CTs also employ multi-angle and multi-irradiation field to reconstruct the object's 3-D information.

SUMMARY OF THE INVENTION

According to an aspect of the present disclosure, a microwave transmission method based on frequency control is provided. The method includes:
  adjusting a microwave in frequency to generate different input microwaves with different frequencies, each of different input microwaves with different frequencies to an input of the single-input multi-output waveguide microwave system;
  assigning the input microwave to a target output port among multiple output ports of the single-input multiple-output waveguide microwave system, according to the frequency of the input microwave; and
  performing microwave output through the target output port.

According to another aspect of the present disclosure, a single-input multiple-output waveguide microwave system is provided. The system includes one input port, a 1-to-N waveguide microwave network, multiple band-pass filters and multiple output ports.

The input port is configured to receive each of different input microwaves with different frequencies:

The 1-to-N waveguide microwave network comprises an input terminal and N output terminals, the input of the 1-to-N waveguide microwave network is coupled to the input port, and the output terminals of the 1-to-N waveguide microwave network are coupled to input terminals of the band-pass filters for adjustment and matching:

The output terminals of the band-pass filters are coupled to the output ports, and are configured to pass or reflect the input microwave according to the frequency of the input microwave.

According to another aspect of the present disclosure, an electronic device is provided. The electronic device includes a storage device and a processor, wherein the storage device is configured to store a computer instruction that may be executable by the processor, and when the computer instruction is executed by the processor, the processor is configured to:
  adjust a microwave in frequency to generate different input microwaves with different frequencies, each of different input microwaves with different frequencies being an input to the single-input multi-output waveguide microwave system;
  assign the input microwave to a target output port among multiple output ports of the single-input multiple-output waveguide microwave system, according to the frequency of the input microwave; and
  perform microwave output through the target output port.

Additional aspects and advantages of embodiments of present disclosure will be given in part in the following descriptions, become apparent in part from the following descriptions, or be learned from the practice of the embodiments of the present disclosure.

BRIEF DESCRIPTION OF THE DRAWINGS

These and other aspects and advantages of embodiments of the present disclosure will become apparent and more readily appreciated from the following descriptions made with reference to the drawings, in which.

DETAILED DESCRIPTION OF THE INVENTION

Figure 1:
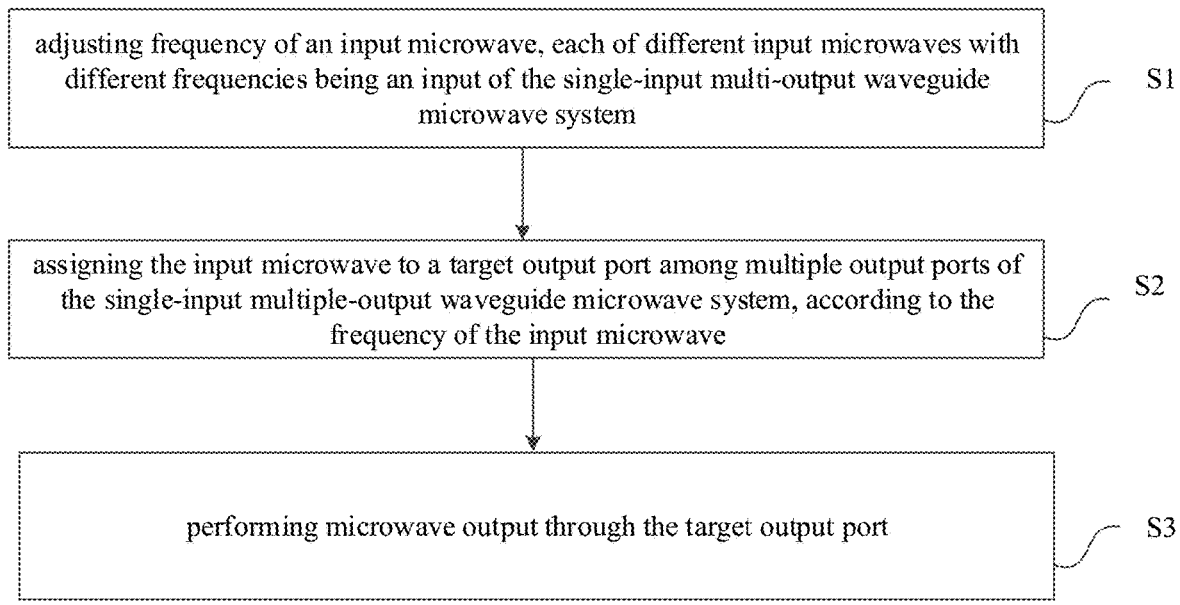
FIG. 1 is a flowchart of a waveguide microwave transmission method based on frequency control according to an embodiment of the present disclosure.

Reference will be made in detail to embodiments of the present disclosure. Examples of the embodiments of the present disclosure will be shown in drawings, in which the same or similar elements and the elements having same or similar functions are denoted by like reference numerals throughout the descriptions. The embodiments described herein according to drawings are explanatory and illustrative, not construed to limit the present disclosure.

At present, most radiotherapy systems employ an irradiation mode with multi-angle and multi-irradiation field, which is usually achieved through mechanically rotating accelerator systems. Exampled with a current advanced helical tomotherapy therapy system (TOMO therapy), which adopts a CT (Computed Tomography) scan-like method for the radiotherapy, a linear accelerator is mounted on a ring frame and may move in a circular motion centered on a treatment bed where a patient is during treatment to realize multi-angle irradiation.

An outstanding disadvantage of mechanically rotating systems using a single accelerator is that time-consuming is longer, which is a common problem of a method of switching the irradiation field through mechanical movement. On the one hand, for stability considerations, a rotating speed of the ring frame cannot be too fast. On the other hand, limitation of a movement speed of the multi-leaf optical grating that adjusts shapes of the irradiation fields also makes the mechanical movement not too fast. The disadvantage is acceptable for conventional irradiations with a low dose rate and a long irradiation time, but unacceptable for FLASH therapy with a high dose rate and an irradiation time less than 1 second. FLASH therapy is a novel radiotherapy treatment by delivering ultrahigh dose rate ($\geq 40$) Gy/s) radiation within a short period ($<1$ s) to trigger FLASH effect which can reduce toxicity to normal tissues. FLASH effect has been demonstrated by numerous radiobiology studies recently and FLASH therapy is believed to be a significant step in the development of radiotherapy with broad application prospects.

Similar to radiotherapy; industrial CTs may also employ manners of mechanically moving accelerators. Because scanning objects of industrial CTs are larger, the corresponding frame will be larger, so the disadvantage of long time-consuming is expressed more obviously.

Therefore, in order to achieve rapid beam irradiation at multiple angles, a system with multiple accelerators is employed. In the entire accelerator system, a power source is one of main components of cost. Multiple accelerators require multiple power inputs. Multiple power sources are required when a traditional method of using one power source to supply one accelerator is employed, which will cause cost of the system to fold increase, and reliability problems caused by RF breakdown of the power sources to be more serious. Power of a single power source is required to be relatively high when the power source is used to supply multiple accelerator simultaneously. Such high-power power sources are usually bulky and have a low repetition frequency, making it difficult to apply to rapid imaging or irradiation.

A microwave transmission method, an apparatus and a single-input multiple-output waveguide microwave system based on frequency control according to the embodiments of the present disclosure are described with reference to the accompany drawings.

FIG. 1 is a flowchart of a microwave transmission method based on frequency control, according to an embodiment of the present disclosure.

Step S1, frequency of an input microwave is adjusted, and each of different input microwaves with different frequencies is an input of the single-input multi-output waveguide microwave system.

Specifically, each of the different input microwaves with different frequencies may be generated within a certain frequency range by a power source.

Step S2, the input microwave is assigned to a target output port among multiple output ports of the single-input multiple-output waveguide microwave system, according to the frequency of the input microwave.

Further, the single-input multiple-output waveguide microwave system includes one input port and multiple output ports. Any one output port only allows an input microwave whose frequency is within a preset frequency range to pass, and reflects an input microwave whose frequency is outside the preset frequency range. The input port is matched with no reflection when the input microwave whose frequency is within a preset frequency range of one output port.

It is appreciated that an input microwave of a certain frequency is input. Each output port among the multiple output ports of the single-input multiple-output waveguide microwave system corresponds to one preset frequency range. The input microwave may be output when the frequency of the input microwave is within the preset frequency range, otherwise it may be reflected. A specific value of the preset frequency range is set according to a specific structure of the waveguide microwave system.

Step S3, microwave output is performed through the target output port.

Specifically, after the target output port is selected, the microwave is output.

With the microwave transmission method based on frequency control proposed in the embodiments of the present disclosure, the frequency of the input microwave is adjusted, and each of the different input microwaves with different frequencies is an input of the single-input multi-output waveguide microwave system. The input microwave is assigned to the target output port among multiple output ports of the single-input multiple-output waveguide microwave system, according to the frequency of the input microwave. The microwave output is performed through the target output port. Thus, a function of performing a selectively matching output from the corresponding output port when adjusting the frequency of the input microwave is realized.

The following describes the single-input multiple-output waveguide microwave system in the embodiments of the present disclosure.

Figure 2:
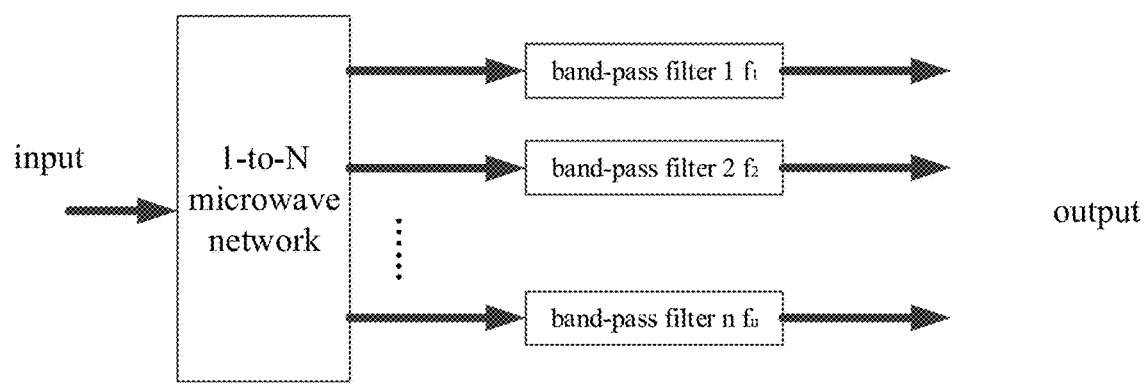
FIG. 2 is a block diagram of a structure of a single-input multi-output waveguide microwave system according to an embodiment of the present disclosure.

FIG. 2 is a schematic diagram of a structure of the single-input multiple-output waveguide microwave system according to an embodiment of the present disclosure.

As illustrated in FIG. 2, the single-input multiple-output microwave system includes one input port, a 1-to-N microwave network, multiple band-pass filters and multiple output ports.

The input port is configured to input each of the different input microwaves with different frequencies.

The 1-to-N waveguide microwave network includes an input terminal and N output terminals. The input of the 1-to-N waveguide microwave network is coupled to the input port, and the output terminals of the 1-to-N waveguide microwave network are coupled to input terminals of the band-pass filters for adjustment and matching:

The output terminals of the band-pass filters are coupled to the output ports and are configured to pass or reflect the input microwave according to the frequency of the input microwave.

The output port is configured to perform microwave output.

The single-input multiple-output (SIMO) waveguide microwave system only has one input port, through which each of the input microwaves with different frequencies may be an input, and has multiple output ports, and the number of output ports may be expanded according to actual requirements.

Further, in embodiments of the present disclosure, the 1-to-N waveguide microwave network may be essentially a multi-port network with a scattering parameter S that satisfies certain conditions. The 1-to-N waveguide microwave network includes an input terminal and N output terminals, and N output branches may be symmetrical. When the (N−1) output branches reflect, the remaining one output terminal of the 1-to-N waveguide microwave network matches the input terminal of the 1-to-N waveguide microwave network with no reflection, and a microwave is transmitted from the input terminal of the 1-to-N waveguide microwave network to the remaining one output terminal of the 1-to-N microwave network.

For example, an S matrix for realizing an ideal function of the above-mentioned 1-to-N waveguide microwave network may be expressed as:

$$S = \begin{bmatrix} -\frac{N-1}{N+1} & \frac{2}{N+1} & & \frac{2}{N+1} \\ \frac{2}{N+1} & -\frac{N-1}{N+1} & \cdots & \frac{2}{N+1} \\ \vdots & & \ddots & \vdots \\ \frac{2}{N+1} & \frac{2}{N+1} & \cdots & -\frac{N-1}{N+1} \end{bmatrix}$$

Further, the band-pass filter is further configured to allow the input microwave to entirely pass when the frequency of the input microwave is within frequency passband of the band-pass filter.

Specifically, the band-pass filter is a microwave device that allows an input microwave in a specific frequency band to pass, but reflects an input microwave in other frequency bands. An ideal band-pass filter may pass an entire input microwave whose frequency is within frequency passband, and may completely reflect an incident microwave whose frequencies is outside the frequency passband. As a specific implementation manner, the band-pass filter may be a resonant cavity having a passing type. When the frequency of the input microwave is consistent with resonant frequency of the resonant cavity, the input microwave may pass the resonant cavity entirely. A cascade of multiple resonant cavities having the passing type may be regarded as an equivalent resonator with more narrowband.

In actual application scenarios, characteristics of the passband filter, such as center frequency, passband width, and transmission efficiency, may affect parameters of the system such as frequency, bandwidth, and loss, so the pass-band filter has a requirement to be designed and optimized. An appropriate bandwidth is employed in the design, not only to allow a certain frequency adjustment error, but also to ensure that passbands between band-pass filters do not overlap each other.

Figure 5:
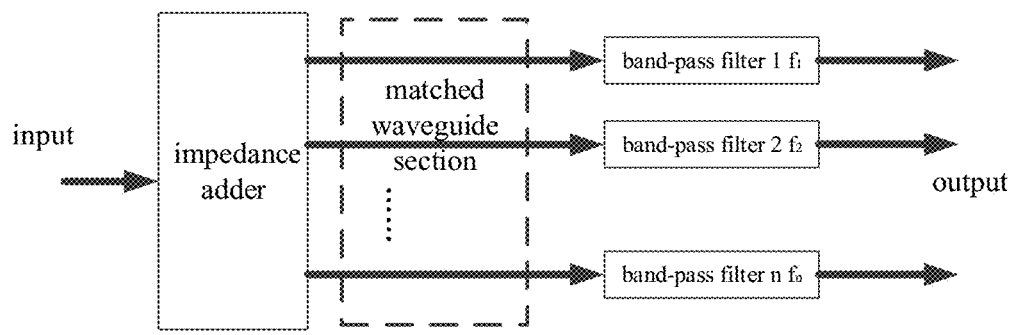
FIG. 5 is a block diagram of a structure of a single-input multi-output waveguide microwave system according to another embodiment of the present disclosure.

Further, the center frequencies of the band-pass filters, such as band-pass filter 1, band-pass filter 2, . . . band-pass filter n as illustrated in FIG. 2 and FIG. 5, are different, and the center frequencies are respectively $f_1$, $f_2$ . . . $f_n$. The frequency of the input microwave is adjustable. When the frequency of the input microwave is consistent with center frequency $f_i$ of a certain resonant cavity, the microwave may be completely transmitted in the corresponding band-pass filter and totally reflected by other band-pass filters. The input terminal of each band-pass filter is coupled to each of the N output terminal of the 1-to-N waveguide microwave network. When the frequency of the input microwave is consistent with the center frequency $f_i$ of the i-th band-pass filter, only the i-th branch is matched with no reflection, and the others (N−1) branches perform entire reflection. The input terminal of the 1-to-N waveguide microwave network is also matched at this time, according to the previously designed 1-to-N waveguide microwave network function, and microwave power is completely transmitted from the input terminal of the 1-to-N waveguide microwave network to the output terminal of the branch where the i-th band-pass filter with the center frequency $f_i$ is located. Thus, rapid switching of different output ports is achieved by controlling the frequency of the power source.

Figure 3:
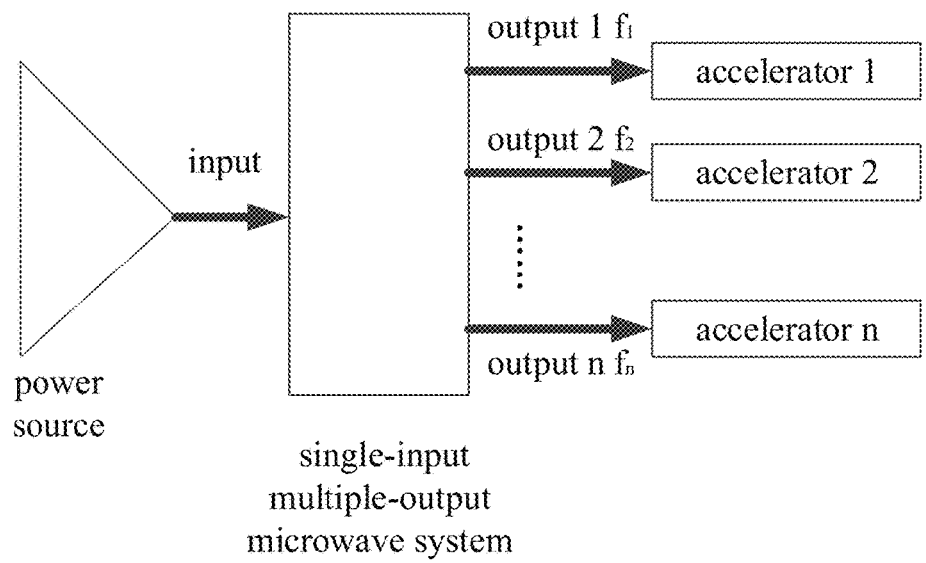
FIG. 3 is a block diagram of a structure of a single-input multi-output waveguide microwave system according to another embodiment of the present disclosure.

As illustrated in FIG. 3, an application scenario of the single-input multiple-output waveguide microwave system is presented. Specifically, the input port may be coupled to a power source, and the power source sends out input microwaves of different frequencies within a certain microwave frequency range.

Furthermore, the multiple output ports are coupled to multiple device loads, and after coupling the power source, a single device load may be supplied with energy, and switching between different device loads may be performed by adjusting input frequency of the power source. For example, as illustrated in FIG. 3, multiple output ports, such as output 1, output 2 . . . output n are coupled to multiple accelerators, such as accelerator 1, accelerator 2, . . . accelerator n.

In embodiments of the present disclosure, multiple accelerators may be coupled to the output ports, and different output ports may be selected for output by adjusting the frequency of the power source to supply different accelerators. Furthermore, when different accelerators are installed at different irradiation angles, rapid switching between multi-angle irradiation fields may be realized. The system is faster than a solution of a mechanically rotating single accelerator, and is lower in cost than a solution with multiple power sources and multiple outputs, also has unique advantages, just like higher reliability and so on.

Figure 4:
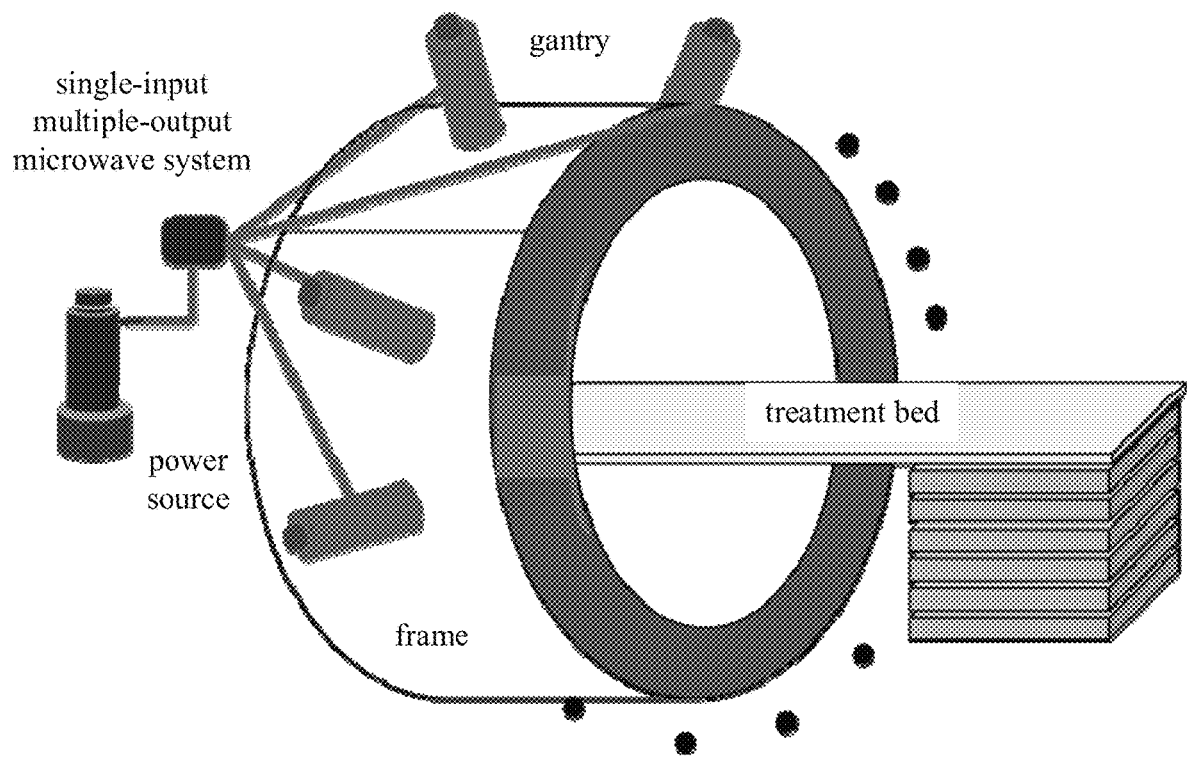
FIG. 4 is a block diagram of a structure of a single-input multi-output waveguide microwave system according to another embodiment of the present disclosure.

As illustrated in FIG. 4, an application scenario of the single-input multiple-output waveguide microwave system is presented. Multiple output ports are coupled to multiple gantries, and input microwaves with different frequencies are emitted out through the power source, and are output at different gantries after passing through the system. The gantries may be mounted on a ring frame and may move in a circular motion centered on a treatment bed. The gantries may be installed at different irradiation angles, which may realize rapid switching between multi-angle irradiation fields. To ensure stability of the system, frequency switching is performed between macro pulses output by the power source, and switching speed may reach order of milliseconds or even microseconds to meet requirements of FLASH radiotherapies. The system is faster than a solution of a mechanically rotating single accelerator, and is lower in cost than a solution with multiple power sources and multiple outputs, also has unique advantages, just like higher reliability and so on.

As illustrated in FIG. 5, a specific structure of the single-input multiple-output waveguide microwave system according to an embodiment of the present disclosure is presented. The mechanism of the 1-to-N waveguide microwave network may include: at least one impedance adder, an input impedance of one port of each impedance adder is equal to the sum of impedances of the other ports of the impedance adder. A matched waveguide section is set between the least one impedance adder and the band-pass filters for impedance matching.

Figure 6:
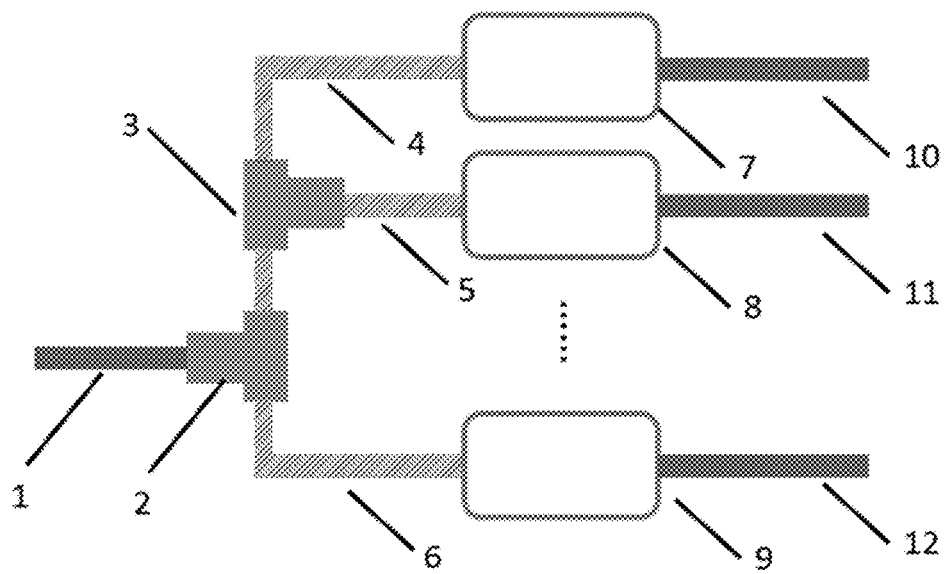
FIG. 6 is a block diagram of a specific structure of a single-input multi-output waveguide microwave system according to an embodiment of the present disclosure.

Combined with FIG. 5 and FIG. 6, in the FIG. 6, 1 is the input port of the single-input multiple-output waveguide microwave system: 2 and 3 are impedance adders. FIG. 6 illustrates only two impedance adders, but the number of the impedance adders may be set according to the number of the output ports of the system in practical applications: 4, 5, and 6 are matched waveguide sections for impedance matching: 7, 8, and 9) are band-pass filters: 10, 11, and 12 are output ports of the system. The number of the matched waveguide sections and band-pass filters is set according to actual number of the output ports of the system. Therefore, the waveguide microwave system of the present disclosure may be discretionarily extended to multiple ports.

The single-input multiple-output waveguide microwave system is mainly composed of the impedance adders, the band-pass filters, and the matched waveguide sections. The various components are described below combined with the FIG. 5 and the FIG. 6.

Figure 9:
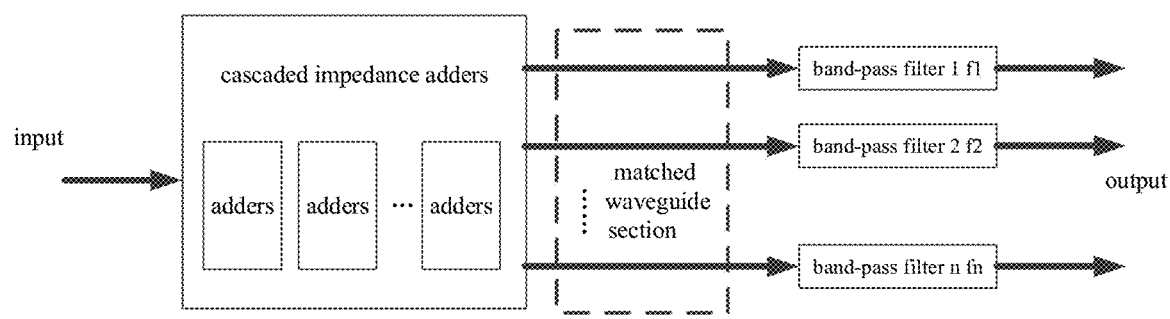
FIG. 9 is a block diagram of a structure of a single-input multi-output waveguide microwave system according to another embodiment of the present disclosure.

In detail, the impedance adder may be essentially a multi-port network with a scattering parameter S that satisfies certain conditions, and has a function that the input impedance of one port in the multi-port network is equal to the sum of the impedances of the remaining ports, thereby calling the impedance adder. When the impedance adders are multiple, multiple impedance adders are cascaded to realize the function of the waveguide microwave system, as shown in FIG. 9. The multiple impedance adders may be multiple basic three-port impedance adders.

Many devices may be used as the band-pass filters. In a specific embodiment of the present disclosure, a resonant cavity having the passing type is taken as an example. An input microwave having a specific resonant frequency may pass completely, and an input microwave deviating from the resonant frequency may be partially or entirely reflected. The characteristics of the resonant cavity such as the resonant frequency, Q value (quality factor) and coupling degree may affect the frequency, bandwidth, loss and other parameters of the system, and the resonant cavity has a requirement to be designed and optimized.

Specifically, the matched waveguide sections for impedance matching are located between the impedance adder and the various band-pass filters. Combine with FIG. 6, waveguide transmission lines between output terminals of the impedance adders and the input terminals of the band-pass filter are used as matched waveguide sections, length of which may be specially designed. The impedance of the band-pass filter when the input microwave is entirely reflected is not a fixed value. In order to output the input microwave at a specific output port, impedance of a certain output terminal of the impedance adder is short-circuited during reflection, that is, 0, so with performing the impedance matching through the matched waveguide section, the impedance of the output terminal of the impedance adder is set as a desired impedance.

Figure 8:
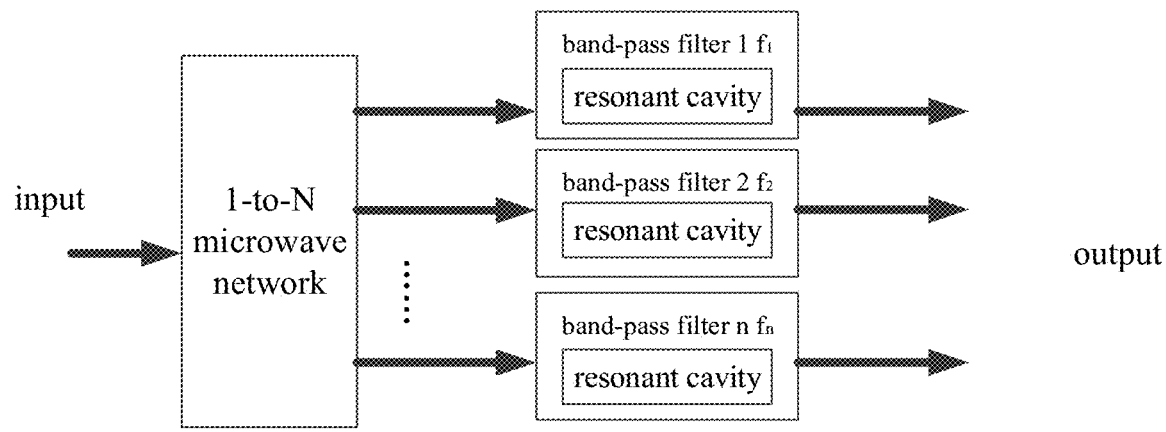
FIG. 8 is a block diagram of a structure of a single-input multi-output waveguide microwave system according to another embodiment of the present disclosure.

Further, the center frequencies of the various band-pass filters are different. Taking the resonant cavity as an example, resonant frequencies of the various cavity are respectively $f_1, f_2 \ldots f_n$, as shown in FIG. 8. The frequency of the microwave output by the power source is adjustable within a certain range. When the frequency of the input microwave is consistent with resonant frequency $f_i$ of a certain resonant cavity, the input microwave may be completely transmitted in the resonant cavity and entirely reflected by other resonant cavities. Through the matched waveguide sections, a normalized impedance matching with no reflection is 1, a normalized impedance of a short circuit with entire reflection is 0. Due to the function of the impedance adder, the normalized impedance of the input terminal of the impedance adder is the sum of the normalized impedances of all output ports, and the value of the normalized impedance is 1+(n−1)*0=1, which means that the input port of the system is matched, and the power is entirely transmitted to the branch where the resonant cavity with the resonant frequency $f_i$ is located. Thus, rapid switching of different output ports is achieved by controlling the frequency of the power source.

With the single-input multiple-output waveguide microwave system proposed in embodiments of the present disclosure, a waveguide microwave system with a single power source supplying energy and a multi-port output is provided, and rapid switching of different output ports is realized by controlling the frequency of the power source. When the output ports are coupled to an accelerator array, the same function of multi-field irradiation as the current single-accelerator frame rotating scanning scheme may be realized, and switching speed between fields is greatly increased on this basis. The number of the output ports may be extended discretionarily and the frequency may be scaled discretionarily.

Figure 7:
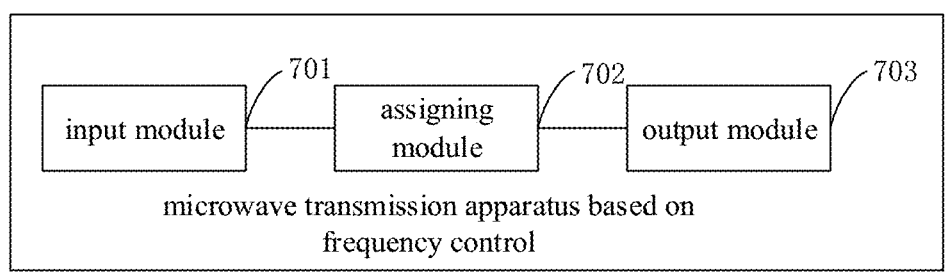
FIG. 7 is a block diagram of a structure of a waveguide microwave transmission apparatus based on frequency control according to an embodiment of the present disclosure.

FIG. 7 is a block diagram of a structure of a waveguide microwave transmission apparatus based on frequency control, according to an embodiment of the present disclosure.

As illustrated in FIG. 7, the waveguide microwave transmission apparatus 10 based on frequency control includes an input module 701, an assigning module 702 and an output module 703.

The input module 701 is configured to adjust frequency of an input microwave, and each of different input microwaves with different frequencies is an input of the single-input multi-output waveguide microwave system.

The assigning module 702 is configured to assign the input microwave to a target output port among multiple output ports of the single-input multiple-output waveguide microwave system, according to the frequency of the input microwave.

The output module 703 is configured to perform microwave output through the target output port.

Further, in an embodiment of the present disclosure, the single-input multiple-output waveguide microwave system includes one input port and multiple output ports. Any one output port only allows the input microwave whose frequency is within a preset frequency range to pass, and reflects the input microwave whose frequency is outside the preset frequency range. The input port is matched with no reflection when the input microwave whose frequency is within a preset frequency range of one output port.

With the waveguide microwave transmission apparatus based on frequency control proposed in the embodiments of the present disclosure, the frequency of the input microwave is adjusted, and each of the different input microwaves with different frequencies is the input of the single-input multi-output waveguide microwave system. The input microwave is assigned to the target output port among multiple output ports of the single-input multiple-output waveguide microwave system, according to the frequency of the input microwave. The microwave output is performed through the target output port. Thus, a function of performing a selectively matching output from the corresponding output port when adjusting the frequency of the input microwave is realized.

According to embodiments of the present disclosure, an electronic device is provided. The electronic device includes a storage device and a processor, and the storage device is configured to store a computer instruction executable by the processor, and when the computer instruction is executed by the processor, the processor is configured to:

adjust frequency of an input microwave, each of different input microwaves with different frequencies being an input of the single-input multi-output waveguide microwave system;

assign the input microwave to a target output port among multiple output ports of the single-input multiple-output waveguide microwave system, according to the frequency of the input microwave; and perform microwave output through the target output port.

Further, in an embodiment of the present disclosure, the single-input multiple-output waveguide microwave system comprises one input port and multiple output ports, one output port allows an input microwave whose frequency is within a preset frequency range to pass, and reflects an input microwave whose frequency is outside the preset frequency range, the input port is matched with no reflection when the input microwave whose frequency is within a preset frequency range of one output port.

In the specification, it is to be understood that terms such as "central," "longitudinal," "lateral," "length," "width," "thickness," "upper," "lower," "front," "rear," "left," "right," "vertical," "horizontal," "top," "bottom," "inner," "outer," "clockwise,", "counterclockwise", "axial", "radial" and "circumferential" should be construed to refer to the orientation as then described or as shown in the drawings under discussion for simplifying the description of the present disclosure, but do not alone indicate or imply that the device or element referred to must have a particular orientation. Moreover, it is not required that the present disclosure is constructed or operated in a particular orientation. Therefore, it cannot be construed as limitation of the present disclosure.

In addition, terms such as "first" and "second" are used herein for purposes of description and are not intended to indicate or imply relative importance or significance or to imply the number of indicated technical features. Thus, the feature defined with "first" and "second" may comprise one or more of this feature. In the description of the present invention, "a plurality of" means at least two, for example, two or three, unless specified otherwise.

In the present invention, unless specified or limited otherwise, the terms "mounted," "connected," "coupled," "fixed" and the like are used broadly, and may be, for example, fixed connections, detachable connections, or integral connections: may also be mechanical or electrical connections: may also be direct connections or indirect connections via intervening structures: may also be inner communications of two elements or interactive relationships of two elements, unless specified otherwise, which can be understood by those skilled in the art according to specific situations.

In the present invention, unless specified or limited otherwise, a structure in which a first feature is "on" or "below" a second feature may include an embodiment in which the first feature is in direct contact with the second feature, and may also include an embodiment in which the first feature and the second feature are not in direct contact with each other, but are contacted via an additional feature formed therebetween. Furthermore, a first feature "on," "above," or "on top of" a second feature may include an embodiment in which the first feature is right or obliquely "on," "above," or "on top of" the second feature, or just means that the first feature is at a height higher than that of the second feature; while a first feature "below," "under," or "on bottom of" a second feature may include an embodiment in which the first feature is right or obliquely "below," "under," or "on bottom of" the second feature, or just means that the first feature is at a height lower than that of the second feature.

Reference throughout this specification to "an embodiment," "some embodiments," "an example," "a specific example," or "some examples," means that a particular feature, structure, material, or characteristic described in connection with the embodiment or example is included in at least one embodiment or example of the present disclosure. Thus, schematic representations of the above terms are not necessarily referring to the same embodiment or example. Furthermore, the particular features, structures, materials, or characteristics may be combined in any suitable manner in one or more embodiments or examples. In addition, without contradiction, different embodiments or examples and the features of the different embodiments or examples described in this specification can be combined and assorted by those skilled in the art.

Although explanatory embodiments have been shown and described, it would be appreciated by those skilled in the art that the above embodiments are exemplary and cannot be construed to limit the present disclosure, and changes, revisions, alternatives, and modifications can be made in the embodiments within scope of the present disclosure.

What is claimed is:

1. A microwave transmission method based on frequency control, comprising:
    adjusting a microwave in frequency to generate different input microwaves with different frequencies, each of different input microwaves with different frequencies being an input to a single-input multi-output waveguide microwave system;
    assigning each of the input microwaves to a target output port among multiple output ports of the single-input multiple-output waveguide microwave system, according to the frequency of each input microwave, wherein the multiple output ports are coupled to multiple accelerators, the multiple accelerators are installed at different irradiation angles, switching between multiple ones of the different irradiation angles is implemented by adjusting the microwave in frequency to generate different input microwaves with different frequencies and selecting different ones of the multiple output ports for output to supply different output microwaves to different accelerators; and
    performing microwave-output through the target output port.

2. The method according to claim 1, wherein the single-input multiple-output waveguide microwave system comprises one input port and the multiple output ports, any one of the multiple output ports allows an input microwave whose frequency is within a preset frequency range to pass among the different input microwaves, and reflects an input microwave whose frequency is outside the preset frequency range among the different input microwaves, the input port is matched without reflection when the input microwave whose frequency is within a preset frequency range of the one output port.

3. A single-input multiple-output waveguide microwave system, comprising one input port, a 1-to-N waveguide microwave network, multiple band-pass filters, multiple output ports and multiple accelerators, wherein, the input port is configured to receive each of different input microwaves with different frequencies;

the 1-to-N waveguide microwave network comprises an input terminal and N output terminals, the input terminal of the 1-to-N waveguide microwave network is coupled to the input port, and the N output terminals of the 1-to-N waveguide microwave network are coupled to input terminals of the multiple band-pass filters, the 1-to-N waveguide microwave network is configured to perform matching;

output terminals of the multiple band-pass filters are coupled to the output ports, and are configured to pass or reflect the input microwaves according to the frequencies of the input microwaves; and the multiple accelerators are coupled to the multiple output ports respectively, wherein the multiple accelerators are installed at different irradiation angles, switching between multiple ones of the different irradiation angles is implemented by adjusting the frequencies of the different input microwaves and selecting different ones of the multiple output ports for output to supply different output microwaves to the different accelerators.

4. The single-input multiple-output waveguide microwave system according to claim 3, wherein, when the multiple band-pass filters coupled to (N−1) output terminals of the 1-to-N waveguide microwave network reflect an input microwave among the different input microwaves, a remaining one output terminal of the 1-to-N waveguide microwave network matches the input terminal of the 1-to-N waveguide microwave network with no reflection, and the input microwave among the different input microwaves is transmitted from the input terminal of the 1-to-N waveguide microwave network to the remaining one output terminal of the 1-to-N waveguide microwave network.

5. The single-input multiple-output waveguide microwave system according to claim 4, wherein, the 1-to-N waveguide microwave network comprises at least one impedance adder, each impedance adder comprises multiple ports, an input impedance of one port of each impedance adder is equal to the sum of impedances of remaining ports other than the one port of said each impedance adder; and multiple impedance adders are cascaded when the impedance adders are multiple.

6. The single-input multiple-output waveguide microwave system according to claim 5, wherein, matched waveguide sections for impedance matching are located between the at least one impedance adder and the multiple band-pass filters.

7. The single-input multiple-output waveguide microwave system according to claim 5, wherein, the waveguide microwave network is formed by the cascaded impedance adders and matched waveguide sections located between the impedance adders and the multiple band-pass filters, and a scattering parameter matrix S of the waveguide microwave network is:

$$S = \begin{bmatrix} -\frac{N-1}{N+1} & \frac{2}{N+1} & \cdots & \frac{2}{N+1} \\ \frac{2}{N+1} & -\frac{N-1}{N+1} & & \frac{2}{N+1} \\ \vdots & & \ddots & \vdots \\ \frac{2}{N+1} & \frac{2}{N+1} & \cdots & -\frac{N-1}{N+1} \end{bmatrix}$$

in which, N is the number of the output terminals of the 1-to-N microwave network formed by the impedance adders.

8. The single-input multiple-output waveguide microwave system according to claim 3, wherein, the input port is coupled to a power source, and the power source generate each of the different input microwaves with different frequencies within a certain microwave frequency range.

9. The single-input multiple-output waveguide microwave system according to claim 3, wherein, each of the multiple band-pass filters is further configured to allow an input microwave among the different input microwaves to pass when the frequency of the input microwave among the different input microwaves is within a frequency passband of a certain band-pass filter.

10. The single-input multiple-output waveguide microwave system according to claim 3, wherein, each of the multiple band-pass filters comprises a resonant cavity of a passing type, and an input microwave among the different input microwaves passes the resonant cavity when the frequency of the input microwave among the different input microwaves is consistent with a resonant frequency of the resonant cavity.

11. The single-input multiple-output waveguide microwave system according to claim 3, wherein, the 1-to-N waveguide microwave network comprises at least one impedance adder, each impedance adder comprises multiple ports, an input impedance of one port of each impedance adder is equal to a sum of impedances of remaining ports other than the one port of each impedance adder.

12. The single-input multiple-output waveguide microwave system according to claim 11, wherein, the 1-to-N waveguide microwave network is formed by cascaded impedance adders and matched waveguide sections located between the impedance adders and the multiple band-pass filters, and a scattering parameter matrix S of the waveguide microwave network is:

$$S = \begin{bmatrix} -\frac{N-1}{N+1} & \frac{2}{N+1} & \cdots & \frac{2}{N+1} \\ \frac{2}{N+1} & -\frac{N-1}{N+1} & & \frac{2}{N+1} \\ \vdots & & \ddots & \vdots \\ \frac{2}{N+1} & \frac{2}{N+1} & \cdots & -\frac{N-1}{N+1} \end{bmatrix}$$

in which, N is the number of the output terminals of the 1-to-N waveguide microwave network formed by the cascaded impedance adders.

13. The single-input multiple-output waveguide microwave system according to claim 11, wherein, matched waveguide sections for impedance matching are located between the at least one impedance adder and the multiple band-pass filters.

14. The single-input multiple-output waveguide microwave system according to claim 11, wherein, multiple impedance adders are cascaded when the impedance adders are multiple.

15. The single-input multiple-output waveguide microwave system according to claim 14, wherein, each of the multiple band-pass filters is a resonant cavity of a passing type, and an input microwave among the different input microwaves passes the resonant cavity when the frequency of the input microwave among the different input microwaves is consistent with a resonant frequency of the resonant cavity.

16. The electronic device according to claim 15, wherein the single-input multiple-output waveguide microwave system comprises one input port and the multiple output ports, one output port of the multiple output ports allows an input microwave whose frequency is within a preset frequency range among the different input microwaves to pass, and reflects an input microwave whose frequency is outside the preset frequency range among the different input microwaves, the input port is matched without reflection when the input microwave whose frequency is within a preset frequency range of the one output port.

17. An electronic device, comprising a non-transitory storage device and a processor, wherein the storage device is configured to store a computer instruction executable by the processor, and when the computer instruction is executed by the processor, the processor is configured to:

adjust a microwave in frequency to generate different input microwaves with different frequencies, each of different input microwaves with different frequencies being an input to a single-input multi-output waveguide microwave system;

assign each of the input microwaves to a target output port among multiple output ports of the single-input multiple-output waveguide microwave system, according to the frequency of each input microwave, wherein the multiple output ports are coupled to multiple accelerators, the multiple accelerators are installed at different irradiation angles, switching between multiple ones of the different irradiation angles is implemented by adjusting the microwave in frequency to generate different input microwaves with different frequencies and selecting different ones of the multiple output ports for output to supply different output microwaves to different accelerators; and perform microwave-output through the target output port.

* * * * *